United States Patent
Kim

(10) Patent No.: US 11,369,511 B2
(45) Date of Patent: Jun. 28, 2022

(54) THERAPEUTIC DEVICE CAPABLE OF INTERACTIVELY CROSS-OUTPUTTING LOW FREQUENCIES OR ULTRASOUND AND HEAT

(71) Applicant: Ceragem Co., Ltd., Chungcheongnam-do (KR)

(72) Inventor: Yong Hee Kim, Chungcheongnam-do (KR)

(73) Assignee: CERAGEM CO., LTD.

(*) Notice: Subject to any disclaimer, the term of this patent is extended or adjusted under 35 U.S.C. 154(b) by 964 days.

(21) Appl. No.: 15/309,277

(22) PCT Filed: May 7, 2015

(86) PCT No.: PCT/KR2015/004535
§ 371 (c)(1),
(2) Date: Feb. 13, 2017

(87) PCT Pub. No.: WO2015/170883
PCT Pub. Date: Nov. 12, 2015

(65) Prior Publication Data
US 2017/0189226 A1    Jul. 6, 2017

(30) Foreign Application Priority Data

May 7, 2014    (KR) .................. 10-2014-0054122

(51) Int. Cl.
*A61N 1/32*    (2006.01)
*A61F 7/00*    (2006.01)
(Continued)

(52) U.S. Cl.
CPC ............ *A61F 7/00* (2013.01); *A61F 7/007* (2013.01); *A61F 7/08* (2013.01); *A61H 23/00* (2013.01);
(Continued)

(58) Field of Classification Search
CPC .... A61F 7/00; A61F 7/007; A61F 7/08; A61F 2007/0086; A61F 2007/0088;
(Continued)

(56) References Cited

U.S. PATENT DOCUMENTS

2007/0106291 A1* 5/2007 Thao ................. A61B 18/14
                                                     606/41
2010/0228304 A1* 9/2010 Kriksunov ............. A61F 7/007
                                                     607/3
(Continued)

FOREIGN PATENT DOCUMENTS

JP    2005065732    3/2005
KR    1020030034685    5/2003
(Continued)

OTHER PUBLICATIONS

International Search Report and Written Opinion issued in Application No. PCT/KR2015/004535, dated Jul. 1, 2015.
(Continued)

*Primary Examiner* — Joanne M Hoffman
*Assistant Examiner* — Yasamin Ekrami
(74) *Attorney, Agent, or Firm* — Norton Rose Fulbright US LLP

(57) ABSTRACT

The present invention relates to a therapeutic device capable of alternatingly outputting a low-frequency wave or an ultrasonic wave and heat, and more particularly, the present invention includes: a heat output unit; and a low-frequency wave output unit which generates a low-frequency wave that is outputted alternatingly with heat outputted by the heat output unit, or includes: a heat output unit; and an ultrasonic wave output unit which generates an ultrasonic wave that is outputted alternatingly with heat outputted by the heat output unit. The present invention provides the therapeutic device capable of alternatingly outputting the low-frequency
(Continued)

(A)

(B)

wave or the ultrasonic wave and the heat, which has the low-frequency wave output unit, the ultrasonic wave output unit, or the low-frequency wave output unit and the ultrasonic wave output unit, and the heat output unit, and maintains a temperature without problems by alternatingly outputting the low-frequency wave or the ultrasonic wave and the heat which are outputted by the output units, respectively, thereby improving user satisfaction.

4 Claims, 10 Drawing Sheets

(51) Int. Cl.
| | | |
|---|---|---|
| *A61N 7/00* | (2006.01) | |
| *A61H 23/02* | (2006.01) | |
| *A61F 7/08* | (2006.01) | |
| *A61N 1/36* | (2006.01) | |
| *A61N 1/04* | (2006.01) | |
| *A61H 23/00* | (2006.01) | |
| *A61F 7/02* | (2006.01) | |

(52) U.S. Cl.
CPC ........... *A61H 23/02* (2013.01); *A61N 1/0492* (2013.01); *A61N 1/32* (2013.01); *A61N 1/36014* (2013.01); *A61N 7/00* (2013.01); *A61F 2007/0086* (2013.01); *A61F 2007/0095* (2013.01); *A61F 2007/0225* (2013.01); *A61N 2007/0078* (2013.01)

(58) Field of Classification Search
CPC ........ A61F 2007/0228; A61N 1/36014; A61N 1/0492; A61N 7/00; A61N 1/32; A61N 2007/0078; A61N 1/321; A61N 2007/0004; A61H 23/02
See application file for complete search history.

(56) References Cited

U.S. PATENT DOCUMENTS

| | | | |
|---|---|---|---|
| 2011/0040235 A1 | 2/2011 | Castel | |
| 2012/0283603 A1 | 11/2012 | Shapiro et al. | |
| 2014/0194958 A1* | 7/2014 | Chabal | A61F 7/02 607/96 |
| 2014/0276247 A1* | 9/2014 | Hall | A61N 1/328 601/2 |

FOREIGN PATENT DOCUMENTS

| | | |
|---|---|---|
| KR | 100553516 | 2/2006 |
| KR | 200412781 | 3/2006 |
| KR | 200412781 Y1 * | 3/2006 |
| KR | 100862648 | 10/2008 |
| KR | 20-2010-0011488 | 11/2010 |
| KR | 20120099941 | 9/2012 |

OTHER PUBLICATIONS

Office Action issued in corresponding European application No. 15788878.5, dated Nov. 20, 2019.
Office Action issued in Corresponding Indian Application No. 201627041134, dated Oct. 22, 2020.

* cited by examiner

THERAPEUTIC DEVICE CAPABLE OF INTERACTIVELY CROSS-OUTPUTTING LOW FREQUENCIES OR ULTRASOUND AND HEAT

TECHNICAL FIELD

The present invention relates to a therapeutic device capable of alternatingly outputting a low-frequency wave or an ultrasonic wave and heat, which is configured to alternatingly output a low-frequency wave or an ultrasonic wave and heat, and as a result, it is possible to achieve therapeutic purposes by using the low-frequency wave or the ultrasonic wave, and to improve user satisfaction as the therapeutic device maintains a temperature without problems.

BACKGROUND ART

As an electrical stimulation therapeutic device in the related art, "a physical therapy and form caring apparatus" is disclosed in Korean Patent No. 10-0862648 (Oct. 2, 2008) (hereinafter, referred to as 'the related art').

The related art has been proposed to provide the physical therapy and form caring apparatus which may disinfect a pad means, which comes into contact with a body and emits a low-frequency wave and heat, by using a liquid such as water, and may maximize a therapeutic effect.

To this end, in the related art, a pad unit, which comes into contact with the body and emits the low-frequency wave and the heat, is fixed by being surrounded by a resin member such as silicone resin having flexibility, and as a result, the pad unit is strong against the liquid such as water such that the pad unit is conveniently disinfected, and the related art intends to provide new feeling to a user and maximize a therapeutic effect by dividing several pad units into two groups and alternatingly outputting the low-frequency waves, and by providing a simultaneous output section and continuously outputting the low-frequency wave.

In addition, the related art is configured to output both of the heat and the low-frequency wave or to selectively output the heat or the low-frequency wave.

However, the method of simultaneously outputting the heat and the low-frequency wave is considered as a regulation object by relevant regulations because of problems with clinical tests and safety, and as a result, the method of simultaneously outputting the heat and the low-frequency wave has problems in respect to commercialization.

In view of the foregoing, there is an acute need for the development of an apparatus which may not simultaneously output the heat and the low-frequency wave or the ultrasonic wave and may simultaneously implement a treatment using stimulation and a fomentation function using heat.

DISCLOSURE

Technical Problem

The present invention has been made in an effort to solve the aforementioned problems, and an object of the present invention is to improve user satisfaction by providing a low-frequency wave output unit or an ultrasonic wave output unit, or a low-frequency wave and ultrasonic wave output unit, and a heat output unit, and by allowing a therapeutic device to maintain a temperature without problems by alternatingly outputting a low-frequency wave or an ultrasonic wave and heat which are outputted by the output units, respectively.

Another object of the present invention is to ensure multifunctionality and improve economic feasibility for both a manufacturer and a consumer by mounting all of the low-frequency wave output unit, the ultrasonic wave output unit, and the heat output unit in a single therapeutic device and selectively operating the low-frequency wave output unit and the ultrasonic wave output unit as necessary.

Yet another object of the present invention is to improve convenience for use by disposing the ultrasonic wave output unit between the low-frequency wave output unit such that the therapeutic device may be used without changing an arrangement structure in accordance with the therapeutic purpose.

Still another object of the present invention is to provide a non-contact alerting means so as to generate warning sound when a pad of the low-frequency wave output unit or the ultrasonic wave output unit is not in contact with or is incompletely in contact with the user's body.

Technical Solution

A therapeutic device capable of alternatingly outputting a low-frequency wave or an ultrasonic wave and heat according to the present invention includes: a heat output unit; and a low-frequency wave output unit which generates a low-frequency wave that is outputted alternatingly with heat outputted by the heat output unit.

The therapeutic device according to the present invention may further include: an ultrasonic wave output unit which generates an ultrasonic wave that is outputted alternatingly with heat outputted by the heat output unit.

A therapeutic device capable of alternatingly outputting a low-frequency wave or an ultrasonic wave and heat according to the present invention includes: a heat output unit; and an ultrasonic wave output unit which generates an ultrasonic wave that is outputted alternatingly with heat outputted by the heat output unit.

The therapeutic device according to the present invention may further include a low-frequency wave output unit which generates a low-frequency wave that is outputted alternatingly with heat outputted by the heat output unit.

The ultrasonic wave output unit according to the present invention may be disposed between the low-frequency wave output unit.

A main body for at least one output unit, among the heat output unit, the low-frequency wave output unit, and the ultrasonic wave output unit, may be provided.

The heat output unit according to the present invention may include a single heating wire or a plurality of heating wires, a first dense portion, where the heating wire is densely disposed at a portion where the low-frequency wave output unit, the ultrasonic wave output unit, or both of the low-frequency wave output unit and the ultrasonic wave output unit are disposed, may be provided in the structure in which the single heating wire is provided, and a second dense portion, where one of the heating wires is densely disposed at a portion where the low-frequency wave output unit, the ultrasonic wave output unit, or both of the low-frequency wave output unit and the ultrasonic wave output unit are disposed, may be provided in the structure in which the plurality of heating wires is provided.

The low-frequency wave output unit according to the present invention may include a plurality of electrode pads, the ultrasonic wave output unit includes a plurality of ultrasonic pads, and a non-contact alerting means, which generates warning sound when there is a defect of contact between a user's body and the electrode pads, the ultrasonic pads, or all of the pads, may be further provided.

The heat output unit according to the present invention may be turned 'off' when a temperature reaches a target temperature, and turned 'on' or 'off' when a temperature is lower than the target temperature so as to perform an output operation alternatingly with the low-frequency wave output unit.

The low-frequency wave output unit according to the present invention may output the low-frequency wave in a pattern in a plurality of continuous cycles, and the heat output unit may be turned 'on' in a idle period between the patterns of the low-frequency wave output unit so as to perform an output operation alternatingly with the low-frequency wave output unit.

Advantageous Effects

The therapeutic device capable of alternatingly outputting the low-frequency wave or the ultrasonic wave and the heat according to the present invention has the low-frequency wave output unit or the ultrasonic wave output unit and the heat output unit, and maintains a temperature without problems by alternatingly outputting the low-frequency wave or the ultrasonic wave and the heat which are outputted by the output units, respectively, thereby improving user satisfaction.

In addition, the present invention may ensure multifunctionality and improve economic feasibility for both a manufacturer and a consumer by mounting all of the low-frequency wave output unit, the ultrasonic wave output unit, and the heat output unit in a single therapeutic device and selectively operating the low-frequency wave output unit and the ultrasonic wave output unit as necessary.

In addition, the present invention may improve convenience for use by disposing the ultrasonic wave output unit between the low-frequency wave output unit such that the therapeutic device may be used without changing an arrangement structure in accordance with the therapeutic purpose.

Further, the present invention has the non-contact alerting means so as to generate warning sound when the pad of the low-frequency wave output unit or the ultrasonic wave output unit is not in contact with or is incompletely in contact with the user's body, thereby improving safety performance in use and a therapeutic effect.

Furthermore, the present invention may be applied to various types of products such as a foot pad, an abdomen pad, and a leg pad, and thus may meet various preferences of consumers by diversifying products.

BEST MODE

Hereinafter, a therapeutic device capable of alternatingly outputting a low-frequency wave or an ultrasonic wave and heat according to the present invention will be described in detail with reference to the accompanying drawings.

Figure 1:
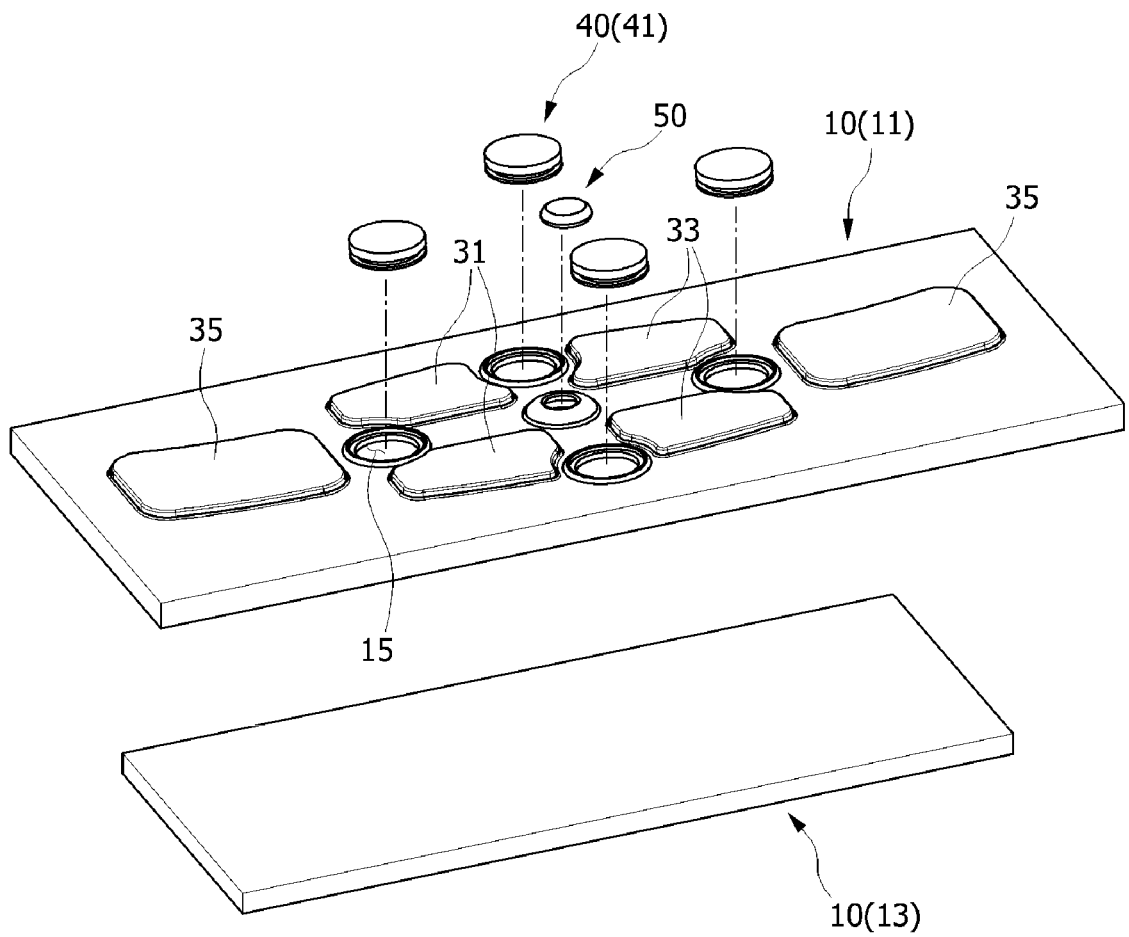
FIG. 1 is a perspective view illustrating a therapeutic device capable of alternatingly outputting a low-frequency wave or an ultrasonic wave and heat according to the present invention.
Figure 2:
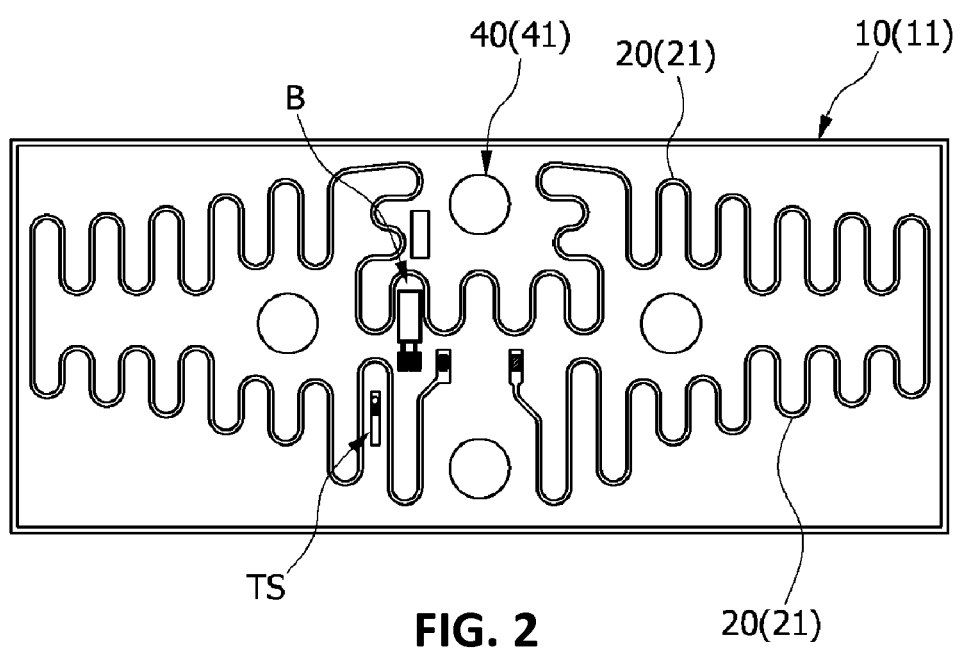
FIG. 2 is a top plan view illustrating an interior arrangement of the therapeutic device according to the present invention.

As illustrated in FIGS. 1 and 2, the therapeutic device capable of alternatingly outputting the low-frequency wave and the heat according to the present invention includes a heat output unit 20, a low-frequency wave output unit 30 and/or an ultrasonic wave output unit 40.

First, as illustrated in FIGS. 1 and 2, for the purpose of manufacturing convenience, the therapeutic device according to the present invention has a main body that includes an upper pad 11, and a lower pad 13 connected, closely attached, mounted, and coupled to the upper pad 11.

The main body may be manufactured as a single body (pad). The present invention is not limited thereto, and the main body may be manufactured by coupling and closely attaching a plurality of separate pads.

The heat output unit 20 is mounted in the main body, and the low-frequency wave output unit 30 and/or the ultrasonic wave output unit 40 is mounted on an outer portion of the main body.

Further, a power source (not illustrated), that is, an SMPS is provided at one side of the main body so as to supply electric power to the therapeutic device. An electric power supply unit (battery or the like) may be mounted in the main body.

In addition, the main body may be manufactured in various forms, and for example, the main body may be manufactured in various forms such as a foot pad shape, an abdomen pad shape, a leg pad shape, and a multi-pad shape, and in addition to the pad shapes, the main body may be manufactured in various forms such as a chair shape, and a mat or mattress shape.

Further, the heat output unit, the low-frequency wave output unit and/or the ultrasonic wave output unit according to the present invention may be applied to a therapeutic device in the form of a glove, and may also be applied to a therapeutic device using a wireless electrode.

Although not illustrated in the attached drawings, in the therapeutic device according to the present invention, the heat output unit, the low-frequency wave output unit and/or the ultrasonic wave output unit may be configured as independent main bodies, that is, pads, respectively, instead of being configured on the single main body.

In this case, the heat output unit may be configured to be attached to and detached from a rear surface or one side of the low-frequency wave output unit or the ultrasonic wave output unit.

In addition, the low-frequency wave output unit and the ultrasonic wave output unit may be configured to be attached to and detached from each other.

As another exemplary embodiment, although not illustrated in the attached drawings, the low-frequency wave output unit and the ultrasonic wave output unit are integrally configured as a single main body (i.e., pad), and the heat output unit may be configured to be attached to and detached from this pad.

However, in the following description, as illustrated in the attached FIGS. 1 and 2, a configuration, in which the heat output unit 20, the low-frequency wave output unit 30, and the ultrasonic wave output unit 40 are configured, as an integrated module, on the main body 10 manufactured in the form of a pad, will be described.

Further, the respective pads of the main body 10 may be made of a soft material when the respective pads need to be deformed in accordance with a use state of the therapeutic device, and the respective pads may be made of a material having rigidity when the respective pads need not to be deformed.

As illustrated in FIGS. 1 and 2, the heat output unit 20 according to the present invention includes a heating wire 21 which is mounted in the upper pad 11 of the main body 10 and disposed in a zigzag pattern in order to form a uniform temperature distribution.

Further, the heating wire 21 of the heat output unit 20 is connected to the power source and generates heat by being supplied with electric power and supplies heat, thereby obtaining a fomentation effect.

In this case, a bi-metal B, as a configuration for constantly maintaining a temperature of the therapeutic device, may be connected to the heating wire 21 of the heat output unit 20, and as a result, it is possible to constantly maintain a temperature of the main body 10 by cutting off electric power when a temperature of the heating wire 21 increases than necessary.

In addition, a temperature sensor TS may be mounted on the main body 10 so as to monitor a temperature of the main body 10 in real time, and the temperature may be controlled by a control unit based on a temperature signal detected by the temperature sensor.

Furthermore, the heating wire 21 of the heat output unit 20 may be disposed in various forms.

Figure 7:
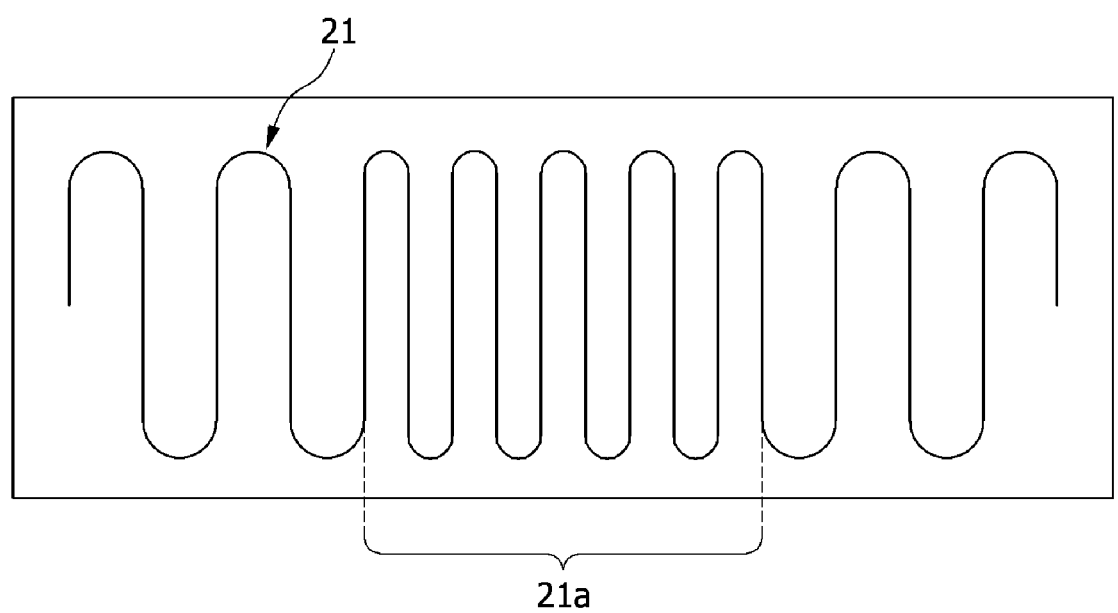
FIGS. 7 and 8 are conceptual views illustrating other exemplary embodiments of a heat output unit according to the present invention.

First, in a case in which the heating wire 21 of the heat output unit 20 is configured as a single wire as illustrated in FIG. 7, the heating wire 21 is disposed in a zigzag pattern, and particularly, a first dense portion 21*a*, where the heating wire 21 is densely disposed, may be provided at a central portion, that is, at a portion where electrode pads 31 and 33 of the low-frequency wave output unit 30 and/or an ultrasonic pad 41 of the ultrasonic wave output unit 40 are disposed.

Figure 8:
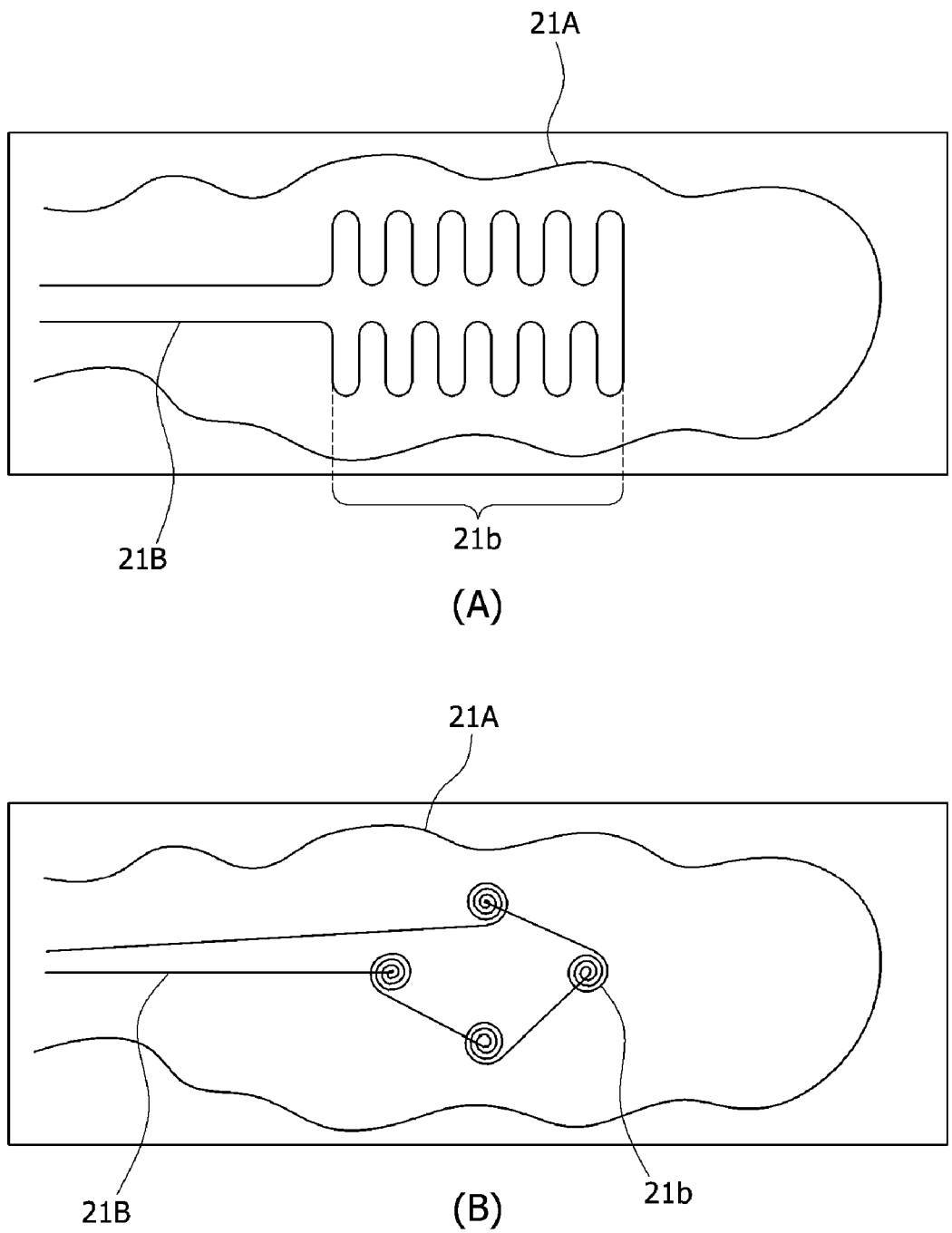

As another exemplary embodiment, in a case in which two heating wires of the heat output unit 20 are disposed as illustrated in FIG. 8A, one heating wire 21A may be disposed in a zigzag pattern on the entire pad of the therapeutic device, and a second dense portion 21*b*, where the other heating wire 21B is densely disposed at the central portion, that is, the pad portions of the output units 30 and 40 are densely disposed, may be provided.

In addition, as illustrated in FIG. 8B, in the second dense portion 21*b*, the heating wire may be densely disposed by being wound in a spiral shape at the pad portions of the output units 30 and 40.

When the therapeutic device is used, the first dense portion 21*a* and the second dense portion 21*b* may quickly heat the pad portions of the output units because the central portion of the pad, that is, the portions, where the electrode pads of the low-frequency wave output unit 30 and/or the ultrasonic pad of the ultrasonic wave output unit 30 are disposed, mainly come into contact with the user's body.

In particular, in a case in which the two heating wires of the heat output unit 20 are disposed and the electrode pads of the low-frequency wave output unit 30 and/or the ultrasonic pad of the ultrasonic wave output unit 40 are made of metal, when the second dense portion 21*b* concentratedly heats the pad portions of the output units and temperatures of the pad portions of the output units reach predetermined temperatures, the heating wire 21B, which constitutes the second dense portion 21*b*, may be turned 'off', and only the other heating wire 21A may be maintained in an 'on' state.

The dense portions 21*a* and 21*b* of the heating wires allow a temperature of a portion, which is in contact with the user's body, to reach the predetermined temperature within short time in comparison with other portions, thereby enabling the therapeutic device to be more efficiently used.

Although not illustrated in the attached drawings, the heat output unit may of course have the two heating wire, and various types of arrangement structures may be implemented by increasing the number of heating wires.

As illustrated in FIGS. 1 and 2, the low-frequency wave output unit 30 according to the present invention includes a plurality of electrode pads 31, 33, and 35 which are mounted on the upper pad 11 of the main body 10 and exposed to the outside, and the electrode pads 31, 33, and 35 are connected to the power source and oscillate frequencies within a predetermined band by being supplied with electric power.

In this case, the respective electrode pads 31, 33, and 35 of the low-frequency wave output unit 30 may oscillate frequencies within different bands or may use a multichannel method in order to apply independent stimulation.

In particular, the therapeutic device according to the present invention is configured to be able to alternatingly output the heat by the heat output unit 20, and the low-frequency wave by the low-frequency wave output unit 30.

Figure 3:
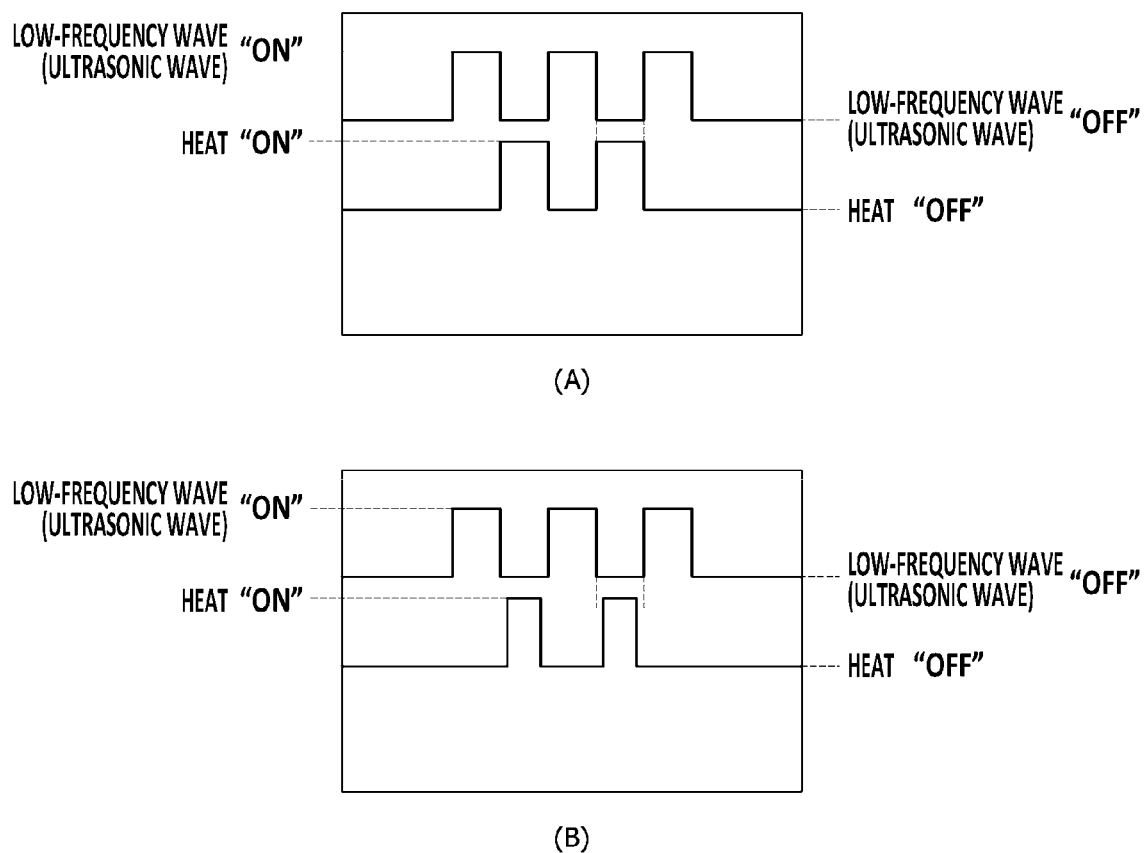
FIGS. 3 and 4 are graphs illustrating states in which the heat and the low-frequency wave (or the ultrasonic wave) is alternatingly outputted by the therapeutic device according to the present invention.

That is, as illustrated in FIG. 3, when the electrode pads 31, 33, and 35 of the low-frequency wave output unit 30 generate the low-frequency waves within the predetermined band, the heat output unit 20 is maintained in the 'off' state, but in contrast, when no low-frequency wave is generated by the electrode pads of the low-frequency wave output unit 30, the heat output unit 20 is in the 'on' state.

That is, the heat output unit 20 is maintained in the 'off' state in a section in which the low-frequency wave within the predetermined band is generated by the low-frequency wave output unit 30, and the heat output unit 20 is maintained in the 'on' state in a section other than the section in which the low-frequency wave is generated.

When only the heat is outputted at all times, the temperature of the therapeutic device is constantly maintained such that a fomentation effect may be obtained, but a therapeutic function by the low-frequency wave may not be carried out while the heat is used, and on the contrary, when only the low-frequency wave is outputted at all times, a fomentation effect by the heat of the therapeutic device may not be expected while the therapeutic function by the low-frequency wave is carried out.

Therefore, in the present invention, the heat and the low-frequency wave, which are outputted by the heat output unit 20 and the low-frequency wave output unit 30, are alternatingly outputted, and as a result, it is possible to perform the therapeutic function by the low-frequency wave, and to maximize the therapeutic effect by the low-frequency wave by constantly maintaining the temperature of the therapeutic device and relaxing muscles at portions required to be treated or stimulated, and it is possible to diversify the therapeutic functions by simultaneously implementing the fomentation effect by the heat.

In this case, FIG. 3A illustrates a case in which the heat by the heat output unit 20 is turned 'off/on' immediately at the moment when the low-frequency wave by the low-frequency wave output unit 30 is turned 'on/off'.

In addition, FIG. 3B illustrates a case in which there is a time difference between a point in time at which the low-frequency wave by the low-frequency wave output unit 30 is turned 'on/off' and a point in time at which the heat by the heat output unit 20 is turned 'off/on'.

In this case, a machine control unit (MCU) provided in a controller stores the output of the low-frequency wave by the low-frequency wave output unit 30, and controls the point in time at which the heat output unit 20 is turned 'on/off'.

That is, when the user selects the output of the low-frequency wave, the MCU stores the output of the low-frequency wave, and controls the heat so as to allow the heat to be in the 'off' state before the 'on' state in which the low-frequency wave is outputted, and to allow the heat to be in the 'on' state after the point in time at which the low-frequency wave is turned 'off', that is, when predetermined time has elapsed.

Here, FIGS. 3A and 3B illustrate that in a case in which the low-frequency wave outputted by the low-frequency wave output unit 30 is outputted in a cycle, the heat is turned 'off/on' at the moment when the low-frequency wave is turned 'on/off' in a cycle between the cycles in which the low-frequency wave is outputted.

Figure 4:
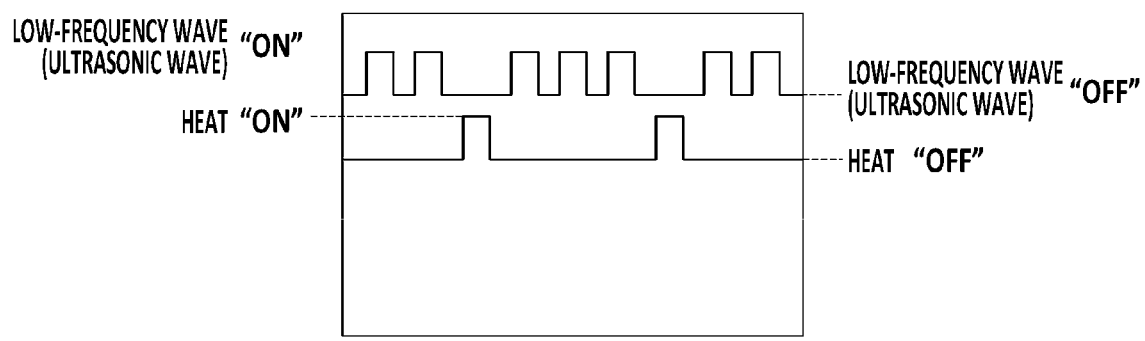

In the case illustrated in FIG. 4, the low-frequency wave by the low-frequency wave output unit 30 is outputted in a pattern continuously in several cycles, and a idle period of time when low-frequency wave is turned 'off' during predetermined time is formed between the respective patterns.

In this case, for example, when the idle period of time is 0.5 second, the heat may be outputted based on setting by the MCU.

Therefore, even in a case in which the low-frequency wave is outputted in a pattern in several cycles, the heat is outputted during the idle period of time between the respective patterns, and the heat is provided during the treatment by the low-frequency wave, and as a result, it is possible to constantly maintain the temperature of the therapeutic device at all times.

Figure 5A:
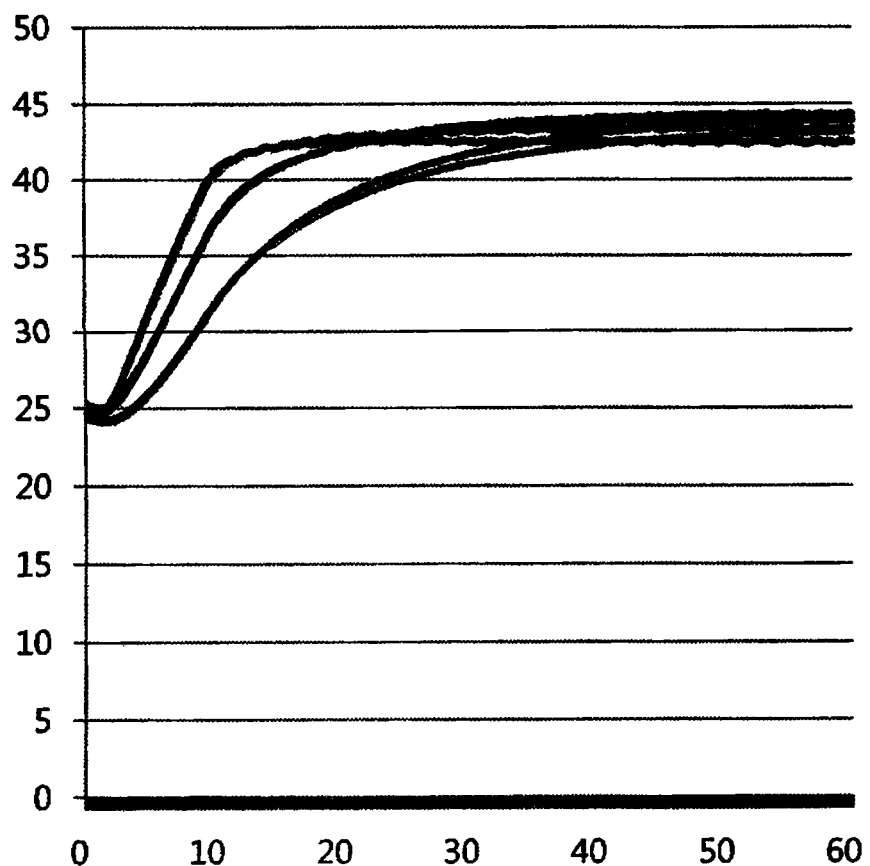
FIGS. 5A and 5B are graphs comparing a case in which the heat is outputted at all times with a case in which the heat and the low-frequency wave are alternatingly outputted in the therapeutic device according to the present invention.
Figure 5B:
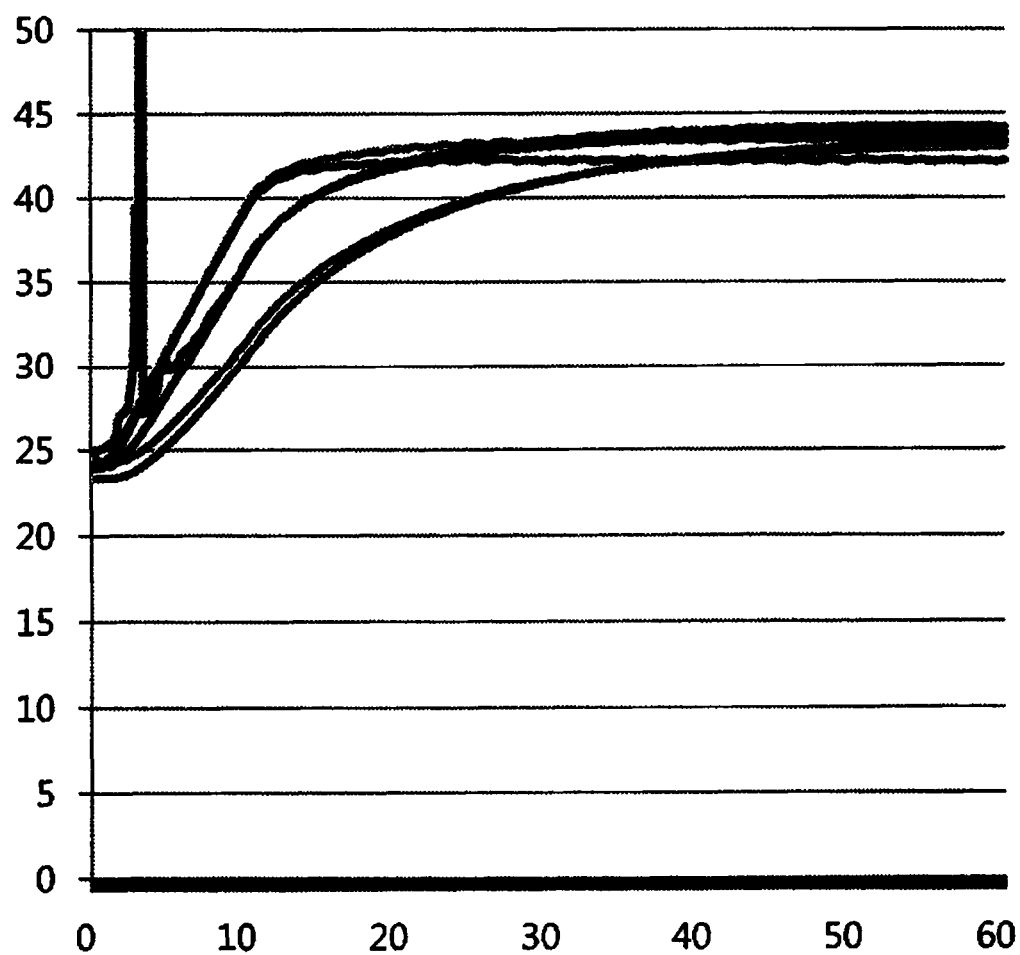

FIGS. 5A and 5B are graphs comparing a case in which only the heat is outputted at all times and a case in which the heat and the low-frequency wave are alternatingly outputted, in respect to the time in which a temperature of the therapeutic device reaches a preset temperature when a maximum preset temperature of the therapeutic device is 45° C.

In addition, the measurement is carried out in a state in which preheating time is excluded to check the time taken to increase the temperature.

First, FIG. 5A illustrates that when only the heat is outputted at all times, it takes about 28 minutes for a temperature of the therapeutic device to reach the preset temperature.

Further, FIG. 5B illustrates that when the heat and the low-frequency wave are alternatingly outputted, it takes about 28 minutes for a temperature of the therapeutic device to reach the preset temperature, which is the same result as illustrated in FIG. 5A.

That is, it can be seen that it takes the same time for a temperature of the therapeutic device to reach the preset temperature in both of the case in which only the heat is outputted at all times as illustrated in FIG. 5A and the case in which the heat and the low-frequency wave are alternatingly outputted as illustrated in FIG. 5B.

Therefore, as described above, the therapeutic device according to the present invention may maximize the therapeutic effect by the low-frequency wave by relaxing a treatment site by using the heat and may also implement the fomentation effect by the heat when the treatment is carried out by the low-frequency wave, and as a result, it is possible to diversify the functions of the therapeutic device, and thus to improve therapeutic efficiency.

As illustrated in FIGS. 1 and 2, the ultrasonic wave output unit 40 according to the present invention includes a plurality of ultrasonic pads 41 which are accommodated in holes 15 formed in the upper pad 11 of the main body 10 and has ultrasonic wave heads mounted therein, and the ultrasonic pads 41 are connected with the power source and generate the ultrasonic waves by being supplied with electric power.

That is, like the low-frequency wave output unit 30, the ultrasonic wave output unit 40 is configured such that the heat by the heat output unit 20 and the ultrasonic wave by the ultrasonic wave output unit 40 are alternatingly outputted.

The operating method for this purpose and the method of controlling the heat according to the output of the ultrasonic wave are identical to the alternating output method by the heat output unit 20 and the low-frequency wave output unit 30, a detailed description thereof will be omitted.

Figure 6A:
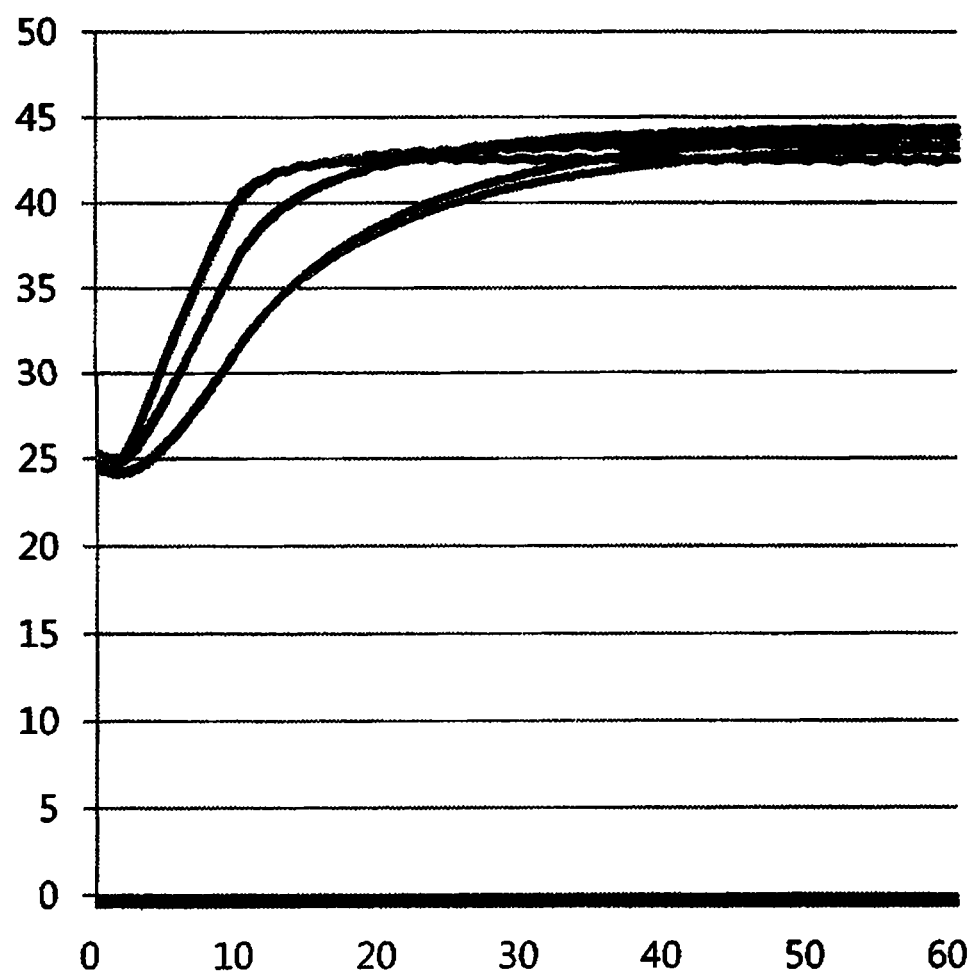
FIGS. 6A and 6B are graphs comparing a case in which the heat is outputted at all times with a case in which the heat and the ultrasonic wave are alternatingly outputted in the therapeutic device according to the present invention.
Figure 6B:
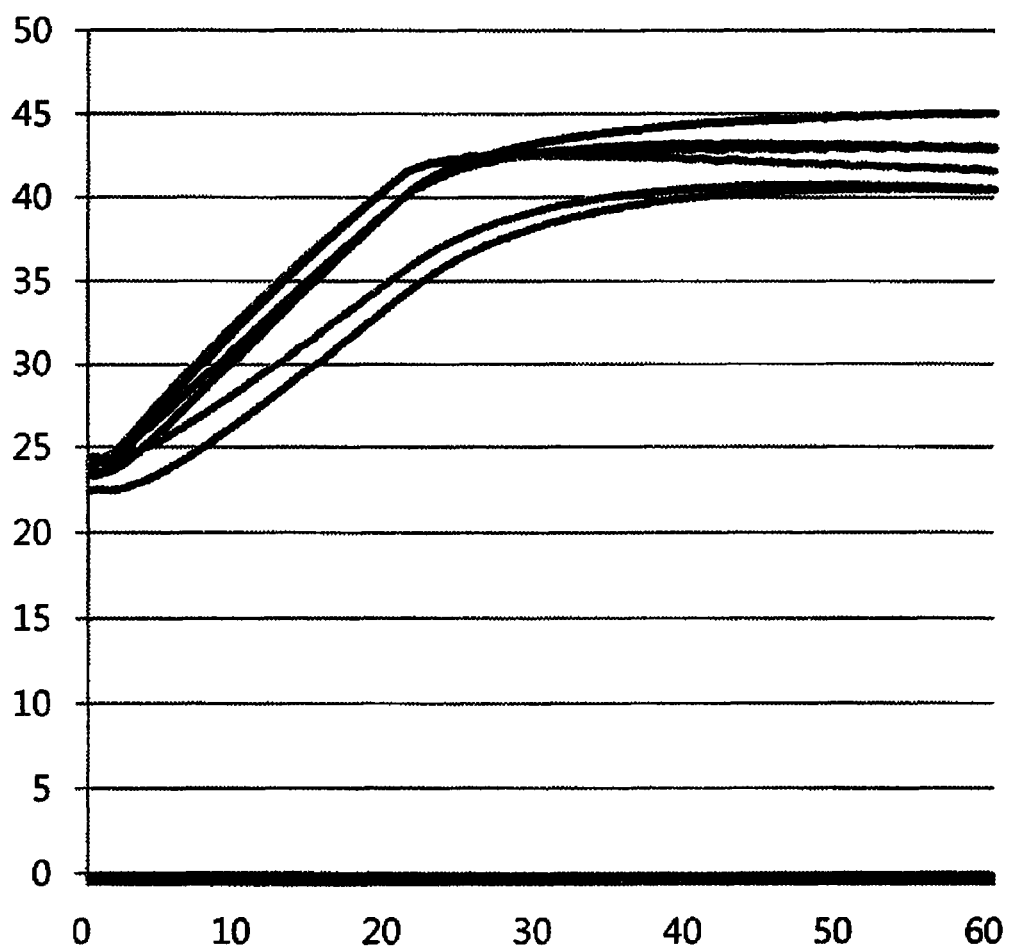

FIGS. 6A and 6B are graphs comparing a case in which only the heat is outputted at all times and a case in which the heat and the ultrasonic wave are alternatingly outputted, in respect to the time a temperature of the therapeutic device reaches a preset temperature in the case of an abdomen or waist pad.

Further, an experimental condition is set to be identical to that of the method of alternatingly outputting the heat and the low-frequency wave.

FIG. 6A illustrates that when only the heat is outputted at all times, it takes about 28 minutes for a temperature of the therapeutic device to reach the preset temperature.

Further, FIG. 6B illustrates that when the heat and the ultrasonic wave are alternatingly outputted, it takes about 42 minutes for a temperature of the therapeutic device to reach the preset temperature, and as a result, the time in which a temperature of the therapeutic device reaches the preset temperature is slightly longer in the case in which the heat and the ultrasonic wave are alternatingly outputted than in the case in which only the heat is outputted at all times.

However, the preset temperature may be constantly maintained when the predetermined time has elapsed, and as a result, when the treatment is carried out by the ultrasonic wave when the predetermined time has elapsed, it is possible to maximize the therapeutic effect by the ultrasonic wave by relaxing a treatment site by using the heat, and also implement the fomentation effect by the heat, and as a result, it is possible to diversify the functions of the therapeutic device, and thus to improve therapeutic efficiency.

As illustrated in FIGS. 5A to 6B, the heat output unit 20 according to the present invention may appropriately maintain a temperature of the pad by being turned 'off' when a temperature of the pad reaches a target temperature, for example, when a temperature of the pad reaches 40° C. to 45° C., and may increase a temperature of the pad to an appropriate temperature by being turned 'on' when a temperature of the pad is decreased to be below the target temperature.

Here, regarding the 'on/off' operation of the heat output unit 20 based on the target temperature, the heat output unit 20 is maintained in the 'off' state when a temperature of the pad reaches the target temperature, regardless of whether the output operations of the low-frequency wave output unit 30 and/or the ultrasonic wave output unit 40.

However, in the case in which the temperature is decreased after the temperature of the pad reaches the target temperature or the case in which the temperature of the pad does not yet reach the target temperature, the operation of turning 'on' the heat output unit 20 means that the heat output unit 20 performs the output operation alternatingly with the low-frequency wave output unit 30 and/or the ultrasonic wave output unit 40 and increases a temperature of the pad to the target temperature.

Therefore, in a case in which a temperature of the pad does not reach the target temperature, the heat output unit 20 is turned 'on' or 'off' and performs the output operation alternatingly with the low-frequency wave output unit and/or the ultrasonic wave output unit until a temperature of the pad reaches the target temperature.

Meanwhile, the therapeutic device according to the present invention may adopt all of the heat output unit 20, the low-frequency wave output unit 30, and the ultrasonic wave output unit 40.

In this case, when the heat by the heat output unit 20 and the low-frequency wave by the low-frequency wave output unit 30 are alternatingly outputted and operated, the ultrasonic wave output unit 40 is maintained in the 'off' state.

In contrast, when the heat by the heat output unit 20 and the ultrasonic wave by the ultrasonic wave output unit 40 are alternatingly outputted and operated, the low-frequency wave output unit 30 is maintained in the 'off' state.

However, only one of the output units may be selectively operated, or the respective output units may sequentially and alternatingly perform the output operations.

Further, the therapeutic device according to the present invention may additionally include a laser output unit in addition to the heat output unit, the low-frequency wave output unit, and the ultrasonic wave output unit 40.

That is, in a case in which all of the heat output unit 20, the low-frequency wave output unit 30, and the ultrasonic wave output unit 40 are applied to the therapeutic device according to the present invention, a variety of functions may be implemented through the aforementioned various driving modes, thereby diversifying effects of the therapeutic device.

In addition, on the consumer side, it is possible to improve satisfaction because various functions may be implemented by the single therapeutic device, and also improve economic feasibility because it is not necessary to separately purchase the therapeutic devices having the functions.

Further, regarding the arrangement structures, the low-frequency wave output unit 30 and the ultrasonic wave output unit 40 according to the present invention may be disposed in various shapes depending on which site of the user's body needs to be subjected to stimulation and whether the therapeutic purposes are achieved.

Among various arrangement structures, the therapeutic device illustrated in the attached FIG. 1 is used to treat an abdomen or a waist part of the user, and this therapeutic device will be described.

First, a total of six electrode pads of the low-frequency wave output unit 30 are disposed, and the arrangement structure thereof will be described below.

That is, a pair of electrode pads is vertically disposed at both sides based on the center of the main body 10, and another pair of electrode pads is disposed at both sides of the main body 10.

In this case, the pair of electrode pads, which is positioned at the left side based on FIG. 1, is referred to as first electrode pads 31, the pair of electrode pads, which is positioned at the right side, is referred to as second electrode pads 33, and the electrode pads, which are positioned at both sides of the first electrode pad and the second electrode pad 33, are referred to as third electrode pads 35.

That is, the first and second electrode pads 31 and 33 are attached to portion adjacent to an origin and an insertion of the rectus abdominis of the user.

In this case, the first and second electrode pads 31 and 33 may be simultaneously contracted, or the second electrode pad 33 may be contracted after the first electrode pad 31 is contracted, and with the alternating stimulation, it is possible to reduce electricity fatigue.

The third electrode pads 35 are attached to the origin of the transverse abdominis of the user, and since the origin of the transverse abdominis is a portion where motor nerves, which control the rectus abdominis and the transverse abdominis, are arranged, it is possible to efficiently contract the rectus abdominis and the transverse abdominis, and reduce a muscle fatigue with the alternating stimulation.

In addition, when an interference phenomenon (IC) occurs by applying intermediate-frequency electric current to the first electrode pad 31 and the third electrode pad 35 which are disposed at the left side based on the center of the main body 10 or to the second electrode pad 33 and the third electrode pad 35 which are disposed at the right side, non-simultaneous muscular contraction occurs by burst, and as a result, it is possible to obtain a physiologic effect similar to voluntary contraction, reduce a fatigue, and induce a function of efficiently strengthening muscles by stimulating core muscles.

In addition, in the case of the abdomen or waist pad, the pad may be attached at a position of the waist and utilized to relieve waist pain for the erector spinae and the peripheral muscles, and as a result, the pad may be utilized in a mode for relieving acute or chronic pain.

Further, the ultrasonic pads 41 of the low-frequency wave output unit 30 are disposed between the electrode pads of the low-frequency wave output unit 30, and in this case, the ultrasonic pads 41 are vertically disposed between the first and second electrode pads 31 and 33, that is, at the central portion of the main body 10, and the ultrasonic pads 41, which are disposed at both sides based on the center of the main body 10, are disposed between the first electrode pads 31 and between the second electrode pads 33.

That is, the arrangement structures among the electrode pads and the ultrasonic pads 41 are disposed at exact positions on the user's body required to be subjected to the stimulation treatment, and as a result, it is possible to improve therapeutic efficiency.

In addition, in a case in which the low-frequency wave output unit 30 and the ultrasonic wave output unit 40 are simultaneously applied, it is possible to implement the arrangement structure that may maximize spatial utilization of the therapeutic device.

The arrangement structure is applied to the abdomen or waist pad, and an optimum arrangement structure for the pad such as a multi-pad or a foot pad may be implemented when treatment sites are changed.

Meanwhile, the therapeutic device according to the present invention may have a non-contact alerting means which generates warning sound when there is a defect of contact between the user's body and the electrode pads 31, 33, and 35 of the low-frequency wave output unit 30, or the ultrasonic pads 41 of the ultrasonic wave output unit 40, or all of the pads.

If the respective pads are not in contact with or are incompletely in contact with the user's body, there is a risk that electrical shock will occur, and as a result, it is necessary to always check whether the respective pads are completely in contact with the user's body.

Therefore, when the respective pads are not in contact with or are incompletely in contact with the user's body, the non-contact alerting means 60 may generate warning sound, thereby enabling the therapeutic device to be safely used and improving the therapeutic effect.

In addition, the non-contact alerting means may generate warning sound only when the electrode pads and the user's body are not in contact with each other or only when the ultrasonic pads and the user's body are not in contact with each other.

In addition, a ceramic 50 illustrated in FIG. 2 is disposed at the central portion of the main body so as to transfer heat and exhibit a function according to material properties.

While the therapeutic device capable of alternatingly outputting the low-frequency wave or the ultrasonic wave and the heat according to the present invention has been described with reference to the accompanying drawings regarding particular shapes and directions, it should be interpreted that the present invention may be variously modified and altered by those skilled in the art, and the modification and the alteration belong to the protection scope of the present invention.

The invention claimed is:

1. A therapeutic device comprising:
   a heat output unit including a first heating wire and a second heating wire, the first heating wire is disposed on an entire pad of the therapeutic device, the second heating wire is disposed at the central portion of the pad and disposed inside of the first heating wire;
   a low-frequency wave output unit including a plurality of electrode pads and configured to generate a low-frequency wave within a predetermined band that is adapted to provide a therapeutic effect to muscles using an alternating output pattern with heat outputted by the heat output unit; and
   an ultrasonic wave output unit including a plurality of ultrasonic pads and configured to generate an ultrasonic wave that is outputted alternatingly with heat outputted by the heat output unit,
   wherein the low-frequency wave output unit and the ultrasonic wave output unit are disposed at the central portion of the pad of the therapeutic device,
   wherein, when the second heating wire concentratedly heats portions of the plurality of electrode pads and the plurality of ultrasonic pads in response to a temperature of the portions of the plurality of electrode pads and the plurality of ultrasonic pads reaching a predetermined temperature, the second heating wire is configured to be turned 'off', and the first heating wire is configured to be maintained in an 'on' state;
   wherein the heat output unit is configured to be turned 'off' in response to a temperature reaching a target temperature, and turned 'on' or 'off' in response to a temperature being lower than the target temperature so as to perform an output operation alternatingly with the low-frequency wave output unit or the ultrasonic wave output unit, and
   wherein the therapeutic device is configured such that when the heat output unit is on, each of the low-frequency wave output unit and the ultrasonic wave output unit are off, and when the low-frequency wave output unit or the ultrasonic wave output unit are on, the heat output unit is off.

2. The therapeutic device of claim 1, wherein each of the plurality of ultrasonic pads of the ultrasonic wave output unit is disposed between two of the plurality of electrode pads of the low-frequency wave output unit.

3. The therapeutic device of claim 1, wherein the therapeutic device comprises a main body for at least one output unit, disposed among the heat output unit, the low-frequency wave output unit, and the ultrasonic wave output unit.

4. The therapeutic device of claim 1, wherein the low-frequency wave output unit or the ultrasonic wave output unit outputs in a pattern in a plurality of continuous cycles, and the heat output unit is turned 'on' in an idle period between the patterns so as to perform an output operation alternatingly with the low-frequency wave or the ultrasonic wave output unit.

* * * * *